United States Patent
Shapiro

(10) Patent No.: US 8,177,827 B2
(45) Date of Patent: May 15, 2012

(54) COOLING DEVICE FOR LOCALLY ANESTHETIZING AN AREA ON THE SURFACE OF THE BODY

(76) Inventor: Oleg Shapiro, Tel Aviv (IL)

( * ) Notice: Subject to any disclaimer, the term of this patent is extended or adjusted under 35 U.S.C. 154(b) by 1076 days.

(21) Appl. No.: 12/062,545

(22) Filed: Apr. 4, 2008

(65) Prior Publication Data

US 2009/0254158 A1   Oct. 8, 2009

(51) Int. Cl.
*A61F 7/00* (2006.01)
*A61F 7/10* (2006.01)
(52) U.S. Cl. .............................. 607/104; 607/96; 62/293
(58) Field of Classification Search .................... 607/96, 607/104
See application file for complete search history.

(56) References Cited

U.S. PATENT DOCUMENTS

| | | | |
|---|---|---|---|
| 2,746,264 A * | 5/1956 | Keyes | ............................. 62/293 |
| 4,205,536 A | 6/1980 | Kasahara | |
| 4,936,487 A * | 6/1990 | Mader et al. | .................. 222/129 |
| 6,648,904 B2 | 11/2003 | Altshuler et al. | |
| 7,597,495 B2 * | 10/2009 | Gueret | .......................... 401/130 |
| 2004/0220518 A1 | 11/2004 | Heruth et al. | |
| 2005/0005626 A1 * | 1/2005 | McMahon | ...................... 62/293 |
| 2007/0198071 A1 | 8/2007 | Ting et al. | |

OTHER PUBLICATIONS

International Search Report mailed Jul. 31, 2009 for PCT/IL2009/000372 filed Apr. 5, 2009.
Written Opinion of the International Searching Authority mailed Jul. 31, 2009 for PCT/IL2009/000372 filed Apr. 5, 2009.

* cited by examiner

*Primary Examiner* — Roy Gibson
*Assistant Examiner* — Jared W Pike
(74) *Attorney, Agent, or Firm* — Martin Fleit; Paul D. Bianco; Fleit Gibbons Gutman Bongini & Bianco PL

(57) ABSTRACT

A cooling device for locally and superficially anesthetizing an area on the surface of the body comprising a coolant fluid contacting a cooler. The cooler is moistened by a disinfection fluid. The cooling device is held in a refrigerator till use, then allowed to warm up to operation temperature. Then, the cooler is applied to the area on the surface of the body.

13 Claims, 3 Drawing Sheets

COOLING DEVICE FOR LOCALLY ANESTHETIZING AN AREA ON THE SURFACE OF THE BODY

FIELD OF THE INVENTION

The present invention generally relates to the field of medical devices. More particularly, the present invention relates to a device for local anesthesia by cooling.

BACKGROUND OF THE INVENTION

Many skin treatments are painful, e.g. receiving injections or cosmetic treatments. To reduce pain, there are different anesthetical treatments which usually involve receiving or applying drugs, and cannot usually be applied by the patients on their own.

SUMMARY

The present invention discloses a cooling device for locally and superficially anesthetizing an area on the surface of the body. The cooling device comprises a coolant within a coolant container and a cooler, in contact with the coolant, and made of heat conducting material for delivering coldness from the coolant to the surface of the body. The cooling device further comprises a temperature indicator for indicating the temperature of the coolant and comparing it to the destined operation temperature. The cooling device further comprises a sponge moistened by a disinfection fluid contained within a disinfection fluid container. The sponge moistens the cooler with the disinfection fluid for disinfection and for improving the contact between the cooler and the skin and avoiding coldness injuries. The cooling device is held below a destined operation temperature before application. It then warms to the destined operation temperature and applied to the area on the surface of the body, which is anesthetized by cooling due to the contact with the cooler.

BRIEF DESCRIPTION OF THE DRAWINGS

The subject matter regarded as the invention will become more clearly understood in light of the ensuing description of embodiments herein, given by way of example and for purposes of illustrative discussion of the present invention only, with reference to the accompanying drawings (Figures, or simply "FIGS."), wherein.

DETAILED DESCRIPTIONS OF SOME EMBODIMENTS OF THE INVENTION

The present invention discloses a cooling device for locally and superficially anesthetizing an area on the surface of the body, before applying a local treatment like an injection. The device allows disinfected and safe home usage.

Figures 1A, 1B:
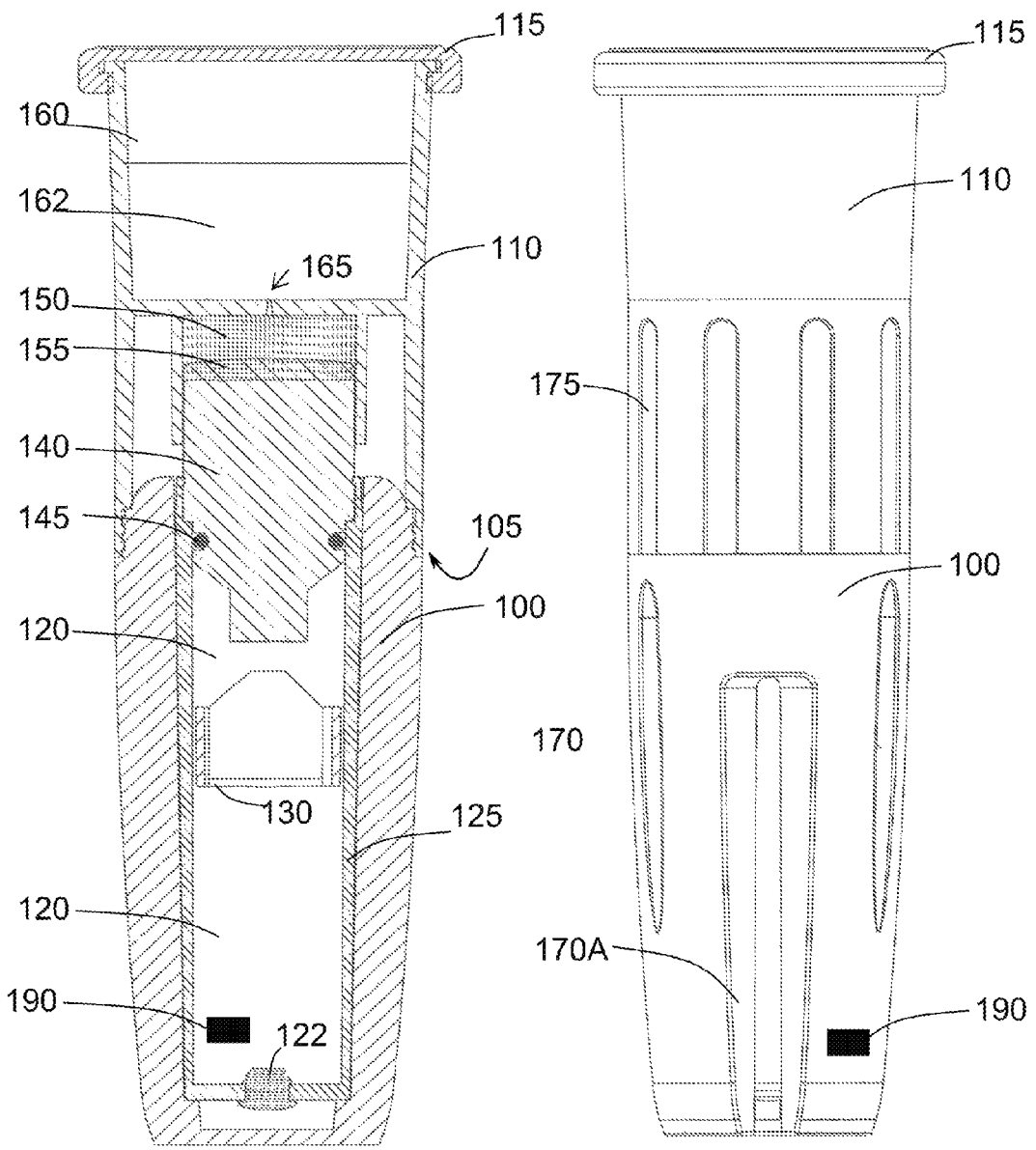
FIG. 1A and FIG. 1B are illustrations of a cooling device for locally anesthetizing an area on the surface of the body according to some embodiments of the invention.

FIG. 1A and FIG. 1B are illustrations of a cooling device for locally anesthetizing an area on the surface of the body according to some embodiments of the invention. FIG. 1A is a cross section of the cooling device, and FIG. 1B is a side view of the cooling device according to some embodiments of the invention. The cooling device comprises a lower part in a case 100, covered by a cap 110 with an upper plug 115. The cap 110 is fastened upon the case 100 (e.g. by screwing 105). The lower part comprises of a coolant container 125 holding a coolant 120 and a float 130 floating in coolant 120. The cooler container 125 is held in the case 100. The coolant container 125 may be filled through a lower opening sealed with a coolant plug 122. A cooler 140 is attached to the upper end of coolant container 125, and the contact between them is sealed with an o-ring 145. The cooler 140 may be made of heat conducting material for delivering coldness from the coolant 120 to the surface of the body that is to be treated. The cap 110 comprises a disinfection fluid container 160 and a sponge 150. Disinfection fluid 162 is held inside container 160, and may wet the sponge 150 through a small hole 165. When the cap 110 is fastened to the case 100, the sponge 150 is held in a squeezed state between the container of the disinfection fluid 160 and the cooler 140, losing a certain volume 155.

Case 100 may comprises gaps 170, 170A in it for allowing the user to see coolant container 125, and cap 110 may comprise gaps 175 in it to allow easier holding.

Figure 2:
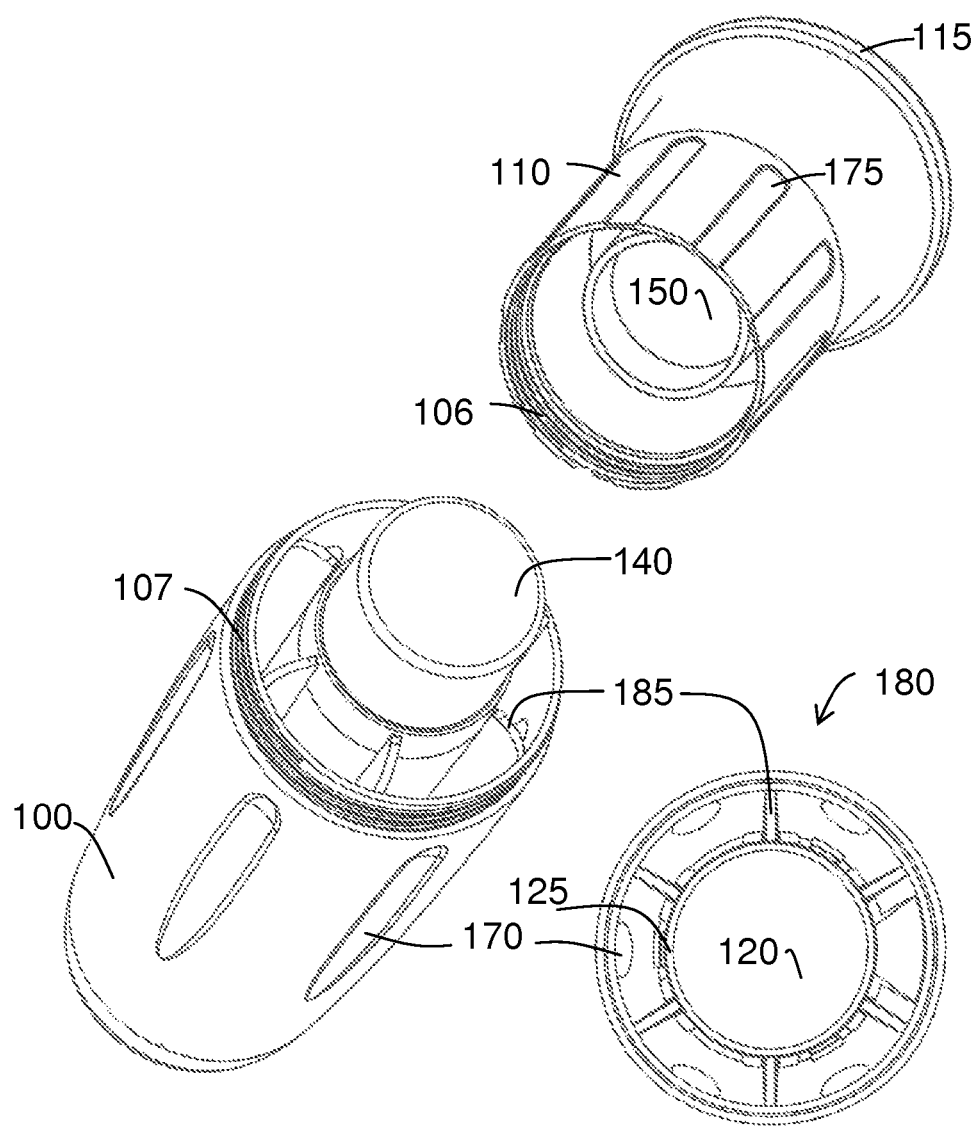
FIG. 2 holds additional illustrations of a cooling device for locally anesthetizing an area on the surface of the body according to some embodiments of the invention.

FIG. 2 holds additional illustrations of a cooling device for locally anesthetizing an area on the surface of the body according to some embodiments of the invention. FIG. 2 shows the lower part and the upper part in a perspective view, and a cross section through the middle of the lower part (180). The upper part comprises cap 110 with gaps 175 and an inner thread 106 (permitting screwing 105), upper plug 115, and sponge 150. The lower part comprises cooler 140 as well as case 100 with gaps 170, a thread 107 (permitting screwing 105), and thin wings 185 for holding coolant container 125 while leaving a heat-insulating air envelope around coolant container 125. Coolant container 125 contains coolant 120.

According to some embodiments of the invention, the contact between case 100 and coolant container 125 may be minimal, so that coolant container 125 is in most of its surface area isolated from case 100 by a layer of air. This may be achieved by case 100 having inner wings, or invaginations that keep the contact to coolant container 125 minimal and allow air to move between case 100 and coolant container 125.

According to some embodiments of the invention, the cooling device is held below a destined operation temperature before application. The cooling device may comprise a temperature indicator 190 for indicating the temperature of the coolant 120, for comparing the temperature of the coolant 120 with the destined operation temperature. The cooler 140 may be substantially in contact with the coolant 120 and with the sponge 150.

According to some embodiments of the invention, a temperature indicator 190 for indicating the temperature of the coolant 120 may be a reversible liquid crystal thermometer. According to some embodiments of the invention, temperature indicator 190 may be a temperature sensitive thermochromic ink or a thermochromic pigment.

According to some embodiments of the invention, the sponge 150 may be any material that may absorb the disinfection fluid 160 and moisten the cooler 140 with the disinfection fluid 160.

According to some embodiments of the invention, disinfection fluid 162 protects the skin against frost injuries. Disinfection fluid 162 mediates the contact between cooler 140 to the skin and reduces the probability of frost injury, as the fluid helps create a larger contact area than the solid cooler 140. Disinfection fluid 162 may have a lower freezing point that coolant 120, and be fluid at storing and operation temperatures. The moistening of cooler 140 with disinfection fluid 162 disinfects the contact area on the surface of the body, improves the contact between cooler 140 and the surface of the body and prevents coldness injuries.

Figure 3:
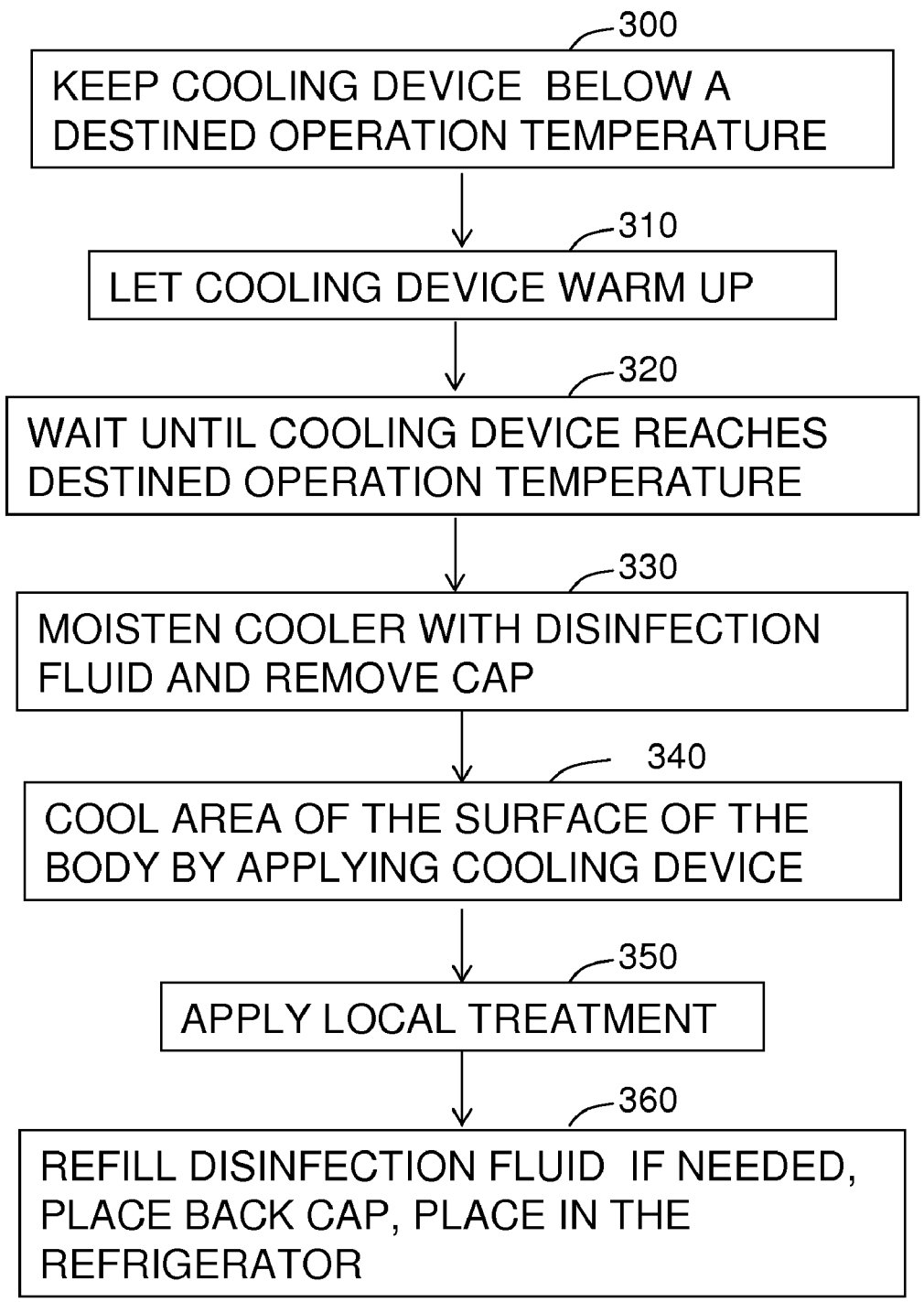
FIG. 3 is a flowchart of a method for locally and superficially anesthetizing an area on the surface of the body before applying a local treatment, according to some embodiments of the invention.

FIG. 3 is a flowchart of a method for locally and superficially anesthetizing an area on the surface of the body before applying a local treatment, according to some embodiments of the invention. The method comprises the steps:

- Keeping the cooling device at least below a destined operation temperature, e.g. in a refrigerator before using it (step 300). The cooling device is cooled to a temperature at least below 0° C.
- Letting the cooling device warm up (step 310), e.g. by taking the cooling device out of the refrigerator, and waiting until the cooling device warms up and reaches the destined operation temperature (step 320).
- Moistening the cooler 140 with disinfection fluid 160 and removing the cap 100 (with sponge 150), thereby exposing the cooler 140 moistened by the disinfection fluid 160 (step 330).
- Cooling the area on the surface of the body by applying the cooler 140 to the skin of the user (step 340), at the location on which the treatment is to be applied.
- Applying treatment (e.g. injection, puncturing, detachment) (step 350).
- Refilling disinfection fluid 160 if needed, placing back the cap 110, placing the cooling device back in the refrigerator (step 360).

The cooling (step 340) locally anesthetizes the area on the surface of the body before the application of the local treatment. The moistening (step 330) of the cooler 140 with the disinfection fluid 160 prevents coldness injuries to the skin.

According to some embodiments of the invention, the method further comprises indicating the temperature of the cooling device to assure the cooling device has reached the destined operation temperature.

According to some embodiments of the invention, letting the cooling device warm up and reach the destined operation temperature (step 310), is carried out by observing a temperature indicator 190. The temperature indicator 190 may comprise a reversible liquid crystal thermometer, a temperature sensitive liquid crystal, a thermochromic pigment, a temperature sensitive thermochromic ink, or indicator of a change of density of coolant 120.

According to some embodiments of the invention operating temperature is between −10° C. and 0° C. Indicating the temperature of the cooling device may take place by any of the following means for indicating the temperature of the coolant 120: temperature sensitive liquid crystal, an indicator of a change of state from solid to liquid (e.g. by appearance or by movement of the floater 130), an indicator of a change of density (e.g. by movement of the floater 130), a change of color of the coolant 120 or of the coolant container 125, an indicator coupled with means for measuring temperature.

According to some embodiments of the invention, disinfection fluid 160 is an alcohol.

According to some embodiments of the invention, cooler material may comprise aluminum, stainless steel or a combination thereof.

According to some embodiments of the invention, coolant 120 materials may be anti-freeze liquids (e.g. mixtures comprising ethylene glycol or propylene glycol), oil (e.g. mixtures comprising alkanes from pentane to dodecane), or silicones.

According to some embodiments of the invention, the cooling device may be held (step 200) in any cooling apparatus other than a refrigerator.

According to some embodiments of the invention, filling the coolant container 125 may take place through the coolant plug 122. According to some embodiments of the invention, filling the coolant container 125 may take place before the cooler 140 is attached to the coolant container 125. According to some embodiments of the invention, filling the container of the disinfection fluid 160 takes place by removing the upper plug 115. After filling, the container of the disinfection fluid 160 is sealed by the upper plug 115.

In the above description, an embodiment is an example or implementation of the inventions. The various appearances of "one embodiment," "an embodiment" or "some embodiments" do not necessarily all refer to the same embodiments.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Reference in the specification to "some embodiments", "an embodiment", "one embodiment" or "other embodiments" means that a particular feature, structure, or characteristic described in connection with the embodiments is included in at least some embodiments, but not necessarily all embodiments, of the inventions.

It is understood that the phraseology and terminology employed herein is not to be construed as limiting and are for descriptive purpose only.

The principles and uses of the teachings of the present invention may be better understood with reference to the accompanying description, figures and examples.

It is to be understood that the details set forth herein do not construe a limitation to an application of the invention.

Furthermore, it is to be understood that the invention can be carried out or practiced in various ways and that the invention can be implemented in embodiments other than the ones outlined in the description above.

It is to be understood that where the claims or specification refer to "a" or "an" element, such reference is not be construed that there is only one of that element.

It is to be understood that where the specification states that a component, feature, structure, or characteristic "may", "might", "can" or "could" be included, that particular component, feature, structure, or characteristic is not required to be included.

Where applicable, although state diagrams, flow diagrams or both may be used to describe embodiments, the invention is not limited to those diagrams or to the corresponding descriptions. For example, flow need not move through each illustrated box or state, or in exactly the same order as illustrated and described.

Methods of the present invention may be implemented by performing or completing manually, automatically, or a combination thereof, selected steps or tasks.

The term "method" may refer to manners, means, techniques and procedures for accomplishing a given task including, but not limited to, those manners, means, techniques and procedures either known to, or readily developed from known manners, means, techniques and procedures by practitioners of the art to which the invention belongs.

The descriptions, examples, methods and materials presented in the claims and the specification are not to be construed as limiting but rather as illustrative only.

Meanings of technical and scientific terms used herein are to be commonly understood as by one of ordinary skill in the art to which the invention belongs, unless otherwise defined.

The present invention can be implemented in the testing or practice with methods and materials equivalent or similar to those described herein.

While the invention has been described with respect to a limited number of embodiments, these should not be construed as limitations on the scope of the invention, but rather as exemplifications of some of the preferred embodiments. Those skilled in the art will envision other possible variations, modifications, and applications that are also within the scope of the invention. Accordingly, the scope of the invention should not be limited by what has thus far been described, but by the appended claims and their legal equivalents.

What is claimed is:

1. A cooling device for locally and superficially anesthetizing an area on the surface of the body, said cooling device held below a destined operation temperature before application, said cooling device comprising:
   a coolant within a coolant container;
   a temperature indicator for indicating the temperature of said coolant, for comparing the temperature of said coolant with said destined operation temperature;
   a cooler made of heat conducting material for delivering coldness from said coolant to said surface of the body, wherein said cooler substantially in contact with said coolant;
   a sponge moistened by a disinfection fluid contained within a disinfection fluid container, said sponge substantially in contact with said cooler and operatively moistening said cooler with said disinfection fluid, wherein said moistening disinfects and improves the contact between said cooler and said surface of the body and prevents coldness injuries;
   wherein said area on the surface of the body is anesthetized by cooling due to the contact with said cooler.

2. The cooling device of claim 1, wherein said disinfection fluid comprises an alcohol.

3. The cooling device of claim 1, wherein said coolant comprises at least one of the following: anti-freeze liquids, ethylene glycol, propylene glycol, oil, alkanes from pentane to dodecane, silicones, mixtures thereof.

4. The cooling device of claim 1, wherein said cooler comprises at least one of the following: aluminum, stainless steel, a combination thereof.

5. The cooling device of claim 1, wherein said temperature indicator comprises at least one of the following: a reversible liquid crystal thermometer, a temperature sensitive liquid crystal, a thermochromic pigment, a temperature sensitive thermochromic ink, combinations thereof.

6. The cooling device of claim 1, wherein said temperature indicator comprises an indicator of a change of density of said coolant.

7. The cooling device of claim 1, wherein said destined operation temperature is between 0° C. and −10° C.

8. A method for locally and superficially anesthetizing an area on the surface of the body before applying a local treatment to said area on the surface of the body, said method comprising:
   keeping a cooling device at least below a destined operation temperature, wherein said cooling device comprises a coolant, a cooler and a disinfection fluid,
   letting said cooling device warm up and reach said destined operation temperature,
   moistening said cooler with said disinfection fluid,
   cooling said area on the surface of the body by applying said cooling device, such that said cooler touches said area on the surface of the body at the place of said applying of local treatment;
   wherein said cooling locally anesthetizes said area on the surface of the body before said local treatment, and wherein said moistening said cooler with said disinfection fluid prevents coldness injuries to the skin.

9. The method of claim 8, wherein said disinfection fluid comprises an alcohol.

10. The method of claim 8, further comprising: indicating the temperature of said cooling device to assure said cooling device has reached said destined operation temperature.

11. The method of claim 8, wherein said letting said cooling device warm up and reach said destined operation temperature is carried out by observing a temperature indicator comprising at least one of the following: a reversible liquid crystal thermometer, a temperature sensitive liquid crystal, a thermochromic pigment, a temperature sensitive thermochromic ink, combinations thereof.

12. The method of claim 8, wherein said letting said cooling device warm up and reach said destined operation temperature is carried out by observing an indicator of a change of density of said coolant.

13. The method of claim 8, wherein said destined operation temperature is between 0° C. and −10° C.

* * * * *